US005919622A

United States Patent [19]

Macho et al.

[11] Patent Number: 5,919,622

[45] **Date of Patent: *Jul. 6, 1999**

[54] SYSTEM FOR THE TEMPERATURE ADJUSTMENT TREATMENT OF LIQUID SAMPLES

[75] Inventors: Heinz Macho, Fürth; Gerhard Bienhaus, Wielenbach, both of Germany

[73] Assignee: Boehringer Mannheim GmbH, D-68305 Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/715,890

[22] Filed: Sep. 19, 1996

[30] Foreign Application Priority Data

Sep. 19, 1995 [DE] Germany ........................... 195 34 632

[51] Int. Cl.$^{6}$ .............................. C12Q 1/68; C12P 19/34; G05D 23/00; B01J 19/08

[52] U.S. Cl. ............................. 435/6; 435/91.2; 422/109; 422/186.19; 422/287

[58] Field of Search ....................... 435/91.2, 6; 422/109, 422/186.19, 287

[56] References Cited

U.S. PATENT DOCUMENTS

| | | | |
|---|---|---|---|
| 5,229,297 | 7/1993 | Schnipelsky | 436/94 |
| 5,408,577 | 4/1995 | Weber | 392/480 |
| 5,504,007 | 4/1996 | Haynes | 435/285.1 |

*Primary Examiner*—Kenneth R. Horlick
*Assistant Examiner*—Joyce Tung
*Attorney, Agent, or Firm*—Nikaido Marmelstein Murray & Oram LLP

[57] ABSTRACT

A system for the temperature adjustment treatment of liquids, especially during the isolation and amplification of nucleic acids with a reusable thermostat element and a disposable heating element has the advantage of a particularly simple means of conducting temperature adjustment treatments. This system facilitates the execution of sample preparation and amplification in a single vessel.

11 Claims, 7 Drawing Sheets

SYSTEM FOR THE TEMPERATURE ADJUSTMENT TREATMENT OF LIQUID SAMPLES

The subject of the invention is a system for the temperature adjustment treatment of nucleic acids, a process for the temperature adjustment treatment of liquid samples and a process for the identification of nucleic acids in a sample.

The setting of a certain temperature in a liquid is an important criteria for reactions which occur with the participation of biologically active components. If the temperature is not correctly set, then it is possible that a certain reaction may not take place at all or occurs to an extent which is undesirable. This is particularly true for all reactions in which enzymes are involved. Enzymes display temperature dependent reaction kinetics. Furthermore, the production of complexes between biological binding partners, e.g. complementary nucleic acids, is temperature dependent. Nucleic acids exist in the single-stranded form above the melting temperature and in the double-stranded form below the melting temperature. In the event that reactions take place consecutively, requiring different temperature regimes, it is necessary to adjust the temperature of the reaction medium.

To date this has been achieved by transporting the reaction vessel containing the reaction mixture back and forth between liquid baths having different temperatures. Because of the fact that the vessel had to be immersed in each bath for a certain period of time, the liquid to be found therein attained the temperature of the liquid in the thermostatic media. After a period of time appropriate for the reaction desired, the vessel containing the liquid was transferred to another liquid bath. These procedures were in themselves very work-intensive and difficult to automate.

More recently devices have been developed in which the vessel containing the liquid to be thermostatted remains confined in the one place but in which the temperature of the thermostatting liquid is adjusted. The disadvantage of this process is the fact that it is relatively time-consuming because the temperature of the entire coolant has to be adjusted. This is particularly disadvantageous in cooling processes.

Temperature adjustment treatment is employed in the nucleic acid diagnostics field in particular. In the polymerase chain reaction (EP-A-201184), for example, the temperature of the thermostatic medium is varied in a cyclic fashion. For these purposes so-called thermocyclers have been described (U.S. Pat. No. 5,038,852 and EP-A-0 488 769). In this process a reaction block made of metal and incorporating recesses for the reaction vessel is heated up and cooled down to effect the temperature adjustment treatment.

In WO 92/78089 a system is described in which the liquid reactants are contained in a closed circulatory system and are transported back and forth between zones with cooling and heating elements. The system required for this procedure is however complex and poorly suited for use in routine work.

In the older, unpublished document DE-A-4409436 a process is described in which a combined heating/cooling element is immersed in the reactant medium and only the temperature of the reactant medium in close proximity to the heating element is adjusted.

During the execution of a temperature adjustment treatment carried out on liquid samples (especially during the polymerase chain reaction), temperatures are employed at which the partial pressure of water is relatively high. Because of this liquid usually condenses on the lid of the reactor vessel. But because this however results in a concentration of the reaction components in the reaction mixture which is not controllable, it has been suggested that heating possibly be incorporated in the lid having the purpose of revaporizing drops of liquid which have condensed on the lid back into the gas phase. Such lid heaters are however so positioned such that they only heat areas which do not extend into the reaction mixture.

The objective of the invention was namely to present an alternative system for use in the temperature adjustment treatment of liquids.

The subject of the invention is a system for the temperature adjustment treatment of nucleic-acid-containing liquids in a vessel which has a reusable thermostat element and a disposable heating element, whereby the heating element is an integral part of the vessel or the vessel lid and is dipped into the liquid during the treatment.

The invention also covers a process for the treatment of nucleic acids in a liquid in the course of which two or more set temperatures are achieved using a thermostat or a heating element, whereby the thermostat element is part of a reusable device and the heating element is part of a disposable device.

Figure 2:
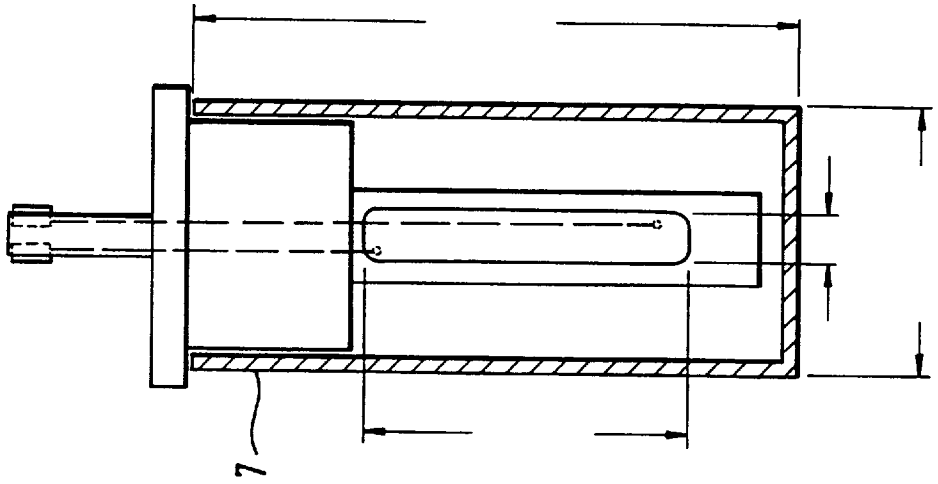
FIG. 2 illustrates the lid set onto a vessel.

The system of invention is intended for use in processes in which a liquid or portions thereof have to be brought to different temperature levels. This is necessary for example when processes which should take place in the liquid, e.g. chemical or preferably enzymatic reactions occur only or advantageously at certain temperatures. Further processes which happen to be temperature sensitive are the above said separation of complementary nucleic acid strands by the warming of the liquid to or the incubation of the liquid at a temperature above the appropriate melting point (Tm) and the creation of hybrids from the nucleic acids which are essentially complementary to each other at temperatures which lie below the melting point, preferably more than 15° C. below the melting point, the so-called hybridization. Another process which requires temperature treatment at elevated temperatures is the degradation of cell compartments. Moreover, elevated temperatures for the targeted destruction of temperature inactivable ingredients present in the liquid, e.g. for the inactivation of enzymes used in the degradation step (proteinases, for example). The system of the invention enables the setting of the necessary or desired temperature in each case regardless of how often the temperature has to be adjusted. It is therefore also possible to repetitively execute several or more than one of these steps consecutively and alternately, e.g. in cycles.

In the sense of this invention, a temperature adjustment treatment of the liquid is taken to mean one in which the liquid is so treated such that processes which should occur in the liquid may take place at differing temperatures. This takes into account both time-dependent temperature profiles as well as location-dependent temperature profiles.

A prominent example for the repeated execution of treatment at differing temperatures is the amplification of nucleic acids by means of the polymerase chain reaction. This reaction has now been described many times in professional circles and in various modified forms.

A prominent example of such a disclosure is U.S. Pat. No. 4,683,202. An essential feature of the polymerase chain reaction (PCR) is the repeated execution of cyclic temperature regimes which includes a treatment at higher temperatures, e.g. between 90 and 95° C., for reduction of double strand nucleic acids which may be present to single strands, a treatment at lower temperatures, e.g. between 50 and 65° C., which promotes the hybridization of primers on the nucleic acid sequences to be amplified and a treatment at medium temperatures, e.g. 70 to 75° C., which favours the optimal elongation of the primers using the nucleic acid to be amplified as a matrix.

The possibility of the variation of the temperature cycles are described in EP-A-0 511 712, for example.

Nucleic acids, which may be subjected to the treatment in the sense of the invention, are all naturally occurring nucleic bases containing biopolymers, derivatives thereof or their analogues which can be obtained by the modification of either the base or its sugar-phosphate backbone. The nucleic acids may be present in the liquid in solution, in cellbound form and may be present in a solid-surface-bound form (immobilized), e.g. to particles.

The nucleic acids are preferably present in the solvated state at least during the steps occurring in the course of the temperature adjustment treatment. It is possible to bring immobilised nucleic acids into solution and vice versa, e.g. by heating a surface-bound nucleic acid with use of an immobilised probe.

All nucleic acid containing liquids are in principle particularly suitable liquids, e.g. samples which are taken directly from their original environment. Especially suitable however are liquids which have undergone a certain amount of preparation, e.g. a step for the removal of certain sample components (i.e. one which may interfere in the method of analysis), the liquidisation of the sample (ie highly viscous samples), a concentration of or dilution of the sample, a lysis step, and also the isolation of the nucleic acids from the original sample (pre-purification).

Liquids such as blood, urine, sputum or smears/swabs in particular are to be taken into consideration.

The vessel in which the temperature adjustment treatment is conducted is preferably fabricated from a material which in the course of the temperature adjustment treatment does not release any of its components into the liquid or deform in the course of the treatment. Particularly suitable in this respect are plastics, e.g. polypropylene or polystyrene. The size of the vessel is chosen such that the sample and any reagents which may possibly be added as well as the heating element fit in. Especially suitable are for example containers derived from Eppendorf-cups but which however preferably do exhibit any material between the cup and the lid. Such containers are commercially available and or may easily be produced by injection-moulding.

A further component of the system is a lid which may be used to close the container. It should be in the position of being able to limit the influx and output of contaminating substances from the vessel e.g. via aerosoles, to within acceptable levels. This too should be fabricated primarily from temperature resistant materials as already stipulated for the containment vessel.

A thermostat element is an object which may be actively brought to a desired temperature and is preferably a cooling element. The cooling element in the sense of this invention is one which is actively cooled and can directly or indirectly transfer heat from the liquid. It does not include the vessel. In a first embodiment of the invention the cooling element is for example a metal block which may be cooled via Peltier (thermoelectric) elements (dry refrigeration) or refrigerated liquids (liquid cooling). If a metal block is employed, then this is preferably fitted to the outer contours of the vessel. A proper fitting can be achieved for example by the making of hollow, cylindrical recesses in the cooling element into which the vessel may be inserted. The better the fit of the cooling element to the external contours of the vessel, the better is the cooling effect. In another example of the embodiment of the invention the cooling element is preferably a metal element which projects through an opening (which is preferably closable using the lid) into the vessel and preferably reaches down below the surface of the liquid. Especially cooling using a Peltier element is preferred in this respect. In this case the cooling element is preferably protected against contamination by the liquid by using a Teflon or polyester film. The film is not regarded as being part of the cooling element because of the fact that it is not reusable. The cooling element can however be in the form of a water bath into which the vessel juts. The heat transfer from the liquid refrigerating medium via the vessel to the reaction mixture is in this case especially direct. A thermostat element in the sense of this invention can certainly however have a capacity to heat, should the temperature adjustment treatment of the liquid require that a certain minimum threshold be respected, which lies significantly, i.e. more than 5K above room temperature. In this event it may be the case that the heat transfer through the thermostat element to the surroundings is so large that maintainance of the lower temperature threshold requires the addition of heat. Nevertheless, the minimum temperature of the thermostat element achieved in the course of the process always lies below the maximum temperature of the heating element attained during the process.

The reusability of the element is taken to mean the possibility of using the same cooling element to treat at least one other liquid. This other liquid has preferably a differing composition to that of the first liquid so that care has to be taken to minimise the contamination of the additional liquid by the first liquid. For this reason the embodiment of the invention in which the cooling element cools the vessel from the outside is preferred.

A heating element in the sense of this invention is an object which is actively heated, the development of its heat being used to warm the liquid subject to the treatment. This can also be taken to mean a multicomponent heater element. The heating element preferably contains a metal wire or a metal foil, e.g. of gold, or a graphite element. Such heating elements are known to professionals skilled in the art. The heating capacity of the heating is designed such that the desired temperature of the liquid is reached in the required time. This can for example be achieved by variation of the size of the heating element or the material of construction employed and the electrical supply.

In the sense of this invention a disposable element is taken to mean an element which after completion of temperature adjustment treatment of a certain liquid is disposed of (thrown away). It is not used for the temperature adjustment treatment of any further liquids which are to be subject to an independent temperature adjustment treatment. In the analysis of such liquids the heating element is thrown away after each analysis. For this reason heating elements having a simple construction and produced at favourable cost are preferred.

An integral component of a construction element in the sense of this invention is a component which without destruction of either the heating element or the construction elements (vessel or lid) cannot be separated from this element. Particularly preferred is the case when the heating element is moulded into the vessel or the lid, this being especially advantageous for the injection-moulding process. In the prime example the heating can be integrated into the vessel. Care should here be taken to ensure that the heating element is localised in the liquid receiving region, namely, for example at the bottom of vessel or at the side walls of the vessel which come into contact with the liquid to be heated. In the preferred embodiment of the invention in which the heating element is an integral component of the lid, the heating element is preferably secured to the inside of the lid and extends into the vessel when the lid is placed on the vessel and preferably until below the level of the liquid. The heating element or connections, for example for electricity, extend away on the outside from the lid and can with the use of coupling elements be connected to a reusable device which supplies the heating element with electricity and possibly for the regulation of the heating capacity.

The dipping of the heating elements into the vessel is in a manner that the liquid receives an adequate amount of heat.

In addition to the system of the invention and its essential components namely, vessel, lid, heating element and cooling element even more suitable elements may be incorporated for the temperature adjustment treatment of liquids and possibly succeeding further processing steps. Construction elements are in particular for the supply of the heating and cooling elements with electricity or coolant respectively, elements for the adjustment of the temperature, elements for the measurement of the temperature, transport units for the vessel, elements for the pipetting of liquids into and out of the vessel and elements to control the whole system. The system preferably incorporates a plurality of vessels and and lids such that it is suitable for the treatment of several liquids in series or parallel (particularly liquids containing nucleic acids).

There are two models possible for the heating and cooling of the liquid. In the first model the heating element is active at intervals, for example, when the liquid is heated over short periods (e.g. only a few fractions of a second) while the cooling is permanently activated. Due to this, differing and consecutive temperature gradients are preferentially set up in the liquid, whereby the temperature in the proximity of the cooling element remains mainly constant whilst the temperature of the liquid near to the heating element varies to a larger extent. In so doing it is possible to achieve a situation whereby, for example, different reactions occur in different locations in the vessel. For example in the case that the heating element is heated to the temperatures necessary for the denaturation of nucleic acids (above the Tm value), denaturation of the nucleic acid only takes place in the proximity of the heating element. Thereafter the denatured nucleic acids can be transported to an area in which hybridization with other nucleic acids can take place. The transport can occur by way of a convection mechanism but diffusion is favoured. In a second particularly preferred embodiment of the invention, the cooling and heating functions are continually activated and preferably remain constant. Over a sufficiently long period of time in this case a stable temperature gradient is achieved which because of the heat conducting capacity of the liquid as well by diffusion and possibly convection is controlled in the liquid. Also in this case different reactions may occur in different locations in the vessel. In this model all components which are to take part in the respective reaction are preferably in solution.

In one preferred model the system consists of a plurality of lids, a plurality of vessels and essentially a thermostatted block as well as elements active in the supply and control of electrical energy for the operation of the heating element.

The thermostat block is preferably a metallic body having receival bore-holes for plastic containers. The thermostatic effect necessary is provided by use of a thermostatted liquid (heat-transfer liquids, circulation refrigeration), employment of Peltier elements or other known thermostatting processes.

The dimensions of the bores for the plastic containers are fitted exactly to the external contours of the plastic vessel because direct contact with the thermostat block is necessary for the effective transfer of heat required.

Such construction features are however known to professionals skilled in the art.

The depth of the bore-holes should preferably be in the relation of 5:1 to the diameter because this ensures that when a temperature gradient is well set up, a mixing of the liquid takes place which is favourable for the system.

The plastic vessel in which the temperature adjustment treatment continually takes place is preferably made of polypropylene and has a wall thickness of less than 1.0 mm (but which depends on the total volume of the reaction mixture).

In the execution of reactions typical in Clinical Chemistry and Nucleic Acid Diagnostics, volumes of less than 1 ml are normally employed. This dictates that the approximate dimensions of the vessel with the lid (which is also manufactured using the injection-moulding process) are 8 mm (inner diameter) and 40 mm in height, respectively.

The disposable heating element consists preferably on the whole of a plastic moulded form, the electrical connections and the heat transfer film. The dimensions of the disposable heating element are fitted to the dimensions of the reaction vessel.

A preferred embodiment of the disposable heating element is one in which a prefabricated arrangement of contacts and heat transfer film is integrated into a plastic component produced by injection-moulding consisting of a lid and a mount.

The heat transfer film is preferably a 20 $\mu$m thick gold film. The injection-moulded plastic component is made of polypropylene. The area of the heating element is preferably 60 mm$^2$ and the lower end of the element extends to the bottom of the vessel in the reaction vessel.

The system detailed above for the temperature adjustment treatment of nucleic acid containing liquids can be employed to advantage in many ways.

Also an object of this invention is therefore a process for the treatment of nucleic acids in a liquid with the application of two or more temperatures using a cooling or heating element whereby the cooling element is an integral part of a reusable device and the heating element is part of a disposable arrangement. The above-mentioned features are also valid for this process. The application of the process of the invention to thermocyclic reactions has proven to be particularly practical. In the course of such processes different reactions take place at different temperatures. The reactions can take place by subjecting the reagents to certain temperatures. This can on the one hand, as described above, be achieved by time-dependent variation of the temperature profile in the reaction mixture and by increasing or decreasing the heating or cooling capacity respectively or, on the other hand, however also by stipulating a constant temperature profile between the heated and cooled regions. Integrades are also conceivable eg achieved by convection in the mixture.

Of importance is that, in accordance with the process of invention, the reactants of the desired reaction are consecutively subjected to different temperatures so that the desired reactions can take place. During the entire period of treatment a cooling effect can be achieved by control of the heating and cooling capacities for example in cyclic reactions so that the reactants are subjected to different reaction parameters in a cyclic fashion and therefore reaction cycles can be conducted consecutively. By subjecting the reaction mixture to a relatively constant temperature gradient, a cyclic treatment occurs favoured by diffusion of the reaction partners from a first spacial volume segment of the reaction mixture having one temperature to a second spacial volume segment having a second temperature. The cyclic course of events occurs by diffusion in a spacial volume segment with one temperature as required by the succeeding reaction (e.g. renewed by the first or a third temperature). Because diffusional processes normally occur relatively slowly, it is preferable to select a rather steep temperature gradient thereby ensuring that the temperature drops between the heating element and the cooling element are limited to a comparatively short path. Typical pathlengths between the heating element and the cooling element are of a few millimeters.

A typical example of a process for the temperature adjustment treatment of nucleic acids is the amplification of nucleic acids or parts thereof. One example of this is the polymerase chain reaction as described in U.S. Pat. No. 4,683,202. One further example is the ligase chain reaction.

A further object of the invention is a process for the detection of nucleic acid in a sample by a) Liberation of the nucleic acid which is to be detected from compartments in which it is contained in a vessel b) Replication of sequence information which is derived from the presence of nucleic acid in the vessel c) Determination of the sequence information whereby the nucleic acid is not removed from the vessel during and between the steps a) to b).

The system of the invention can in so doing be used to significantly simplify the nucleic acid determination procedure. Particularly preferred is the case when the liquid is not transported within the vessel from one location to the other (excepting mixing procedures).

The liberation of the nucleic acids can take place in principle by means which are known. Usual treatments consist of the lysis of cell walls, e.g. with suitable reagents such as proteinase K, detergents or alkali or/and heat. This results in the salvation of the nucleic acids and makes them accessable for reagents which further process them. This step takes place in a vessel which is inert under the conditions of the reaction and the succeeding steps b), e.g. polypropylene. In the same vessel sequence information which is derived from the presence of nucleic acid is replicated e.g. by amplification of a segment of the nucleic acid liberated. This can occur using the polymerase chain reaction.

The term sequence information is taken to mean a sequence of bases eg one (nucleotide sequence) which is part of or the entirety of nucleic acid to be determined.

In principle though the sequence information can be contained in a nucleotide which has been coupled by cross-linking to the nucleic acid to be determined and finally replicated. This can for example be to do with a so-called signal amplification. For the object of the invention it is essential that the reactions taking place in step a) and b) occur in the same vessel. Step b) can for example be initiated when the nucleic acid containing liquid in the vessel is subjected to a temperature adjustment treatment with the aid of the above-mentioned reusable thermostat element, in particular the cooling element, and the disposable heating element. This can preferably occur when the vessel during steps a) and b) is stored in the reusable cooling element and for the execution of step b), the disposable heating element is introduced into the vessel. If the disposable heating element is integrated into the lid, this can be already situated on the vessel during step a) and be engaged in the heat treatment and also be engaged after release of the nucleic acid for the purposes of heat treating.

The determination of the sequence information can in principle occur by the use of procedures known to professionals skilled in the art e.g. by transferring the reaction mixture from step b) into a container in which the nucleic acids produced preferably in the course of a hybridisation reaction can be determined. One possible experimental procedure employs the so-called sandwich principle as described in EP-B-0 079 139. This procedure uses a capture probe complementary to a first part of the replicated sequence information which is either or can be bound to a solid-phase support and a detector probe which is labelled and is complementary to another part of the replicated sequence information. The production of the complex of probe and replicated sequence information containing nucleic acid is interpretated as being an indication of the presence of nucleic acids in the sample. The avoidance of the transfer of nucleic acid from one vessel to the other markedly reduces the risk of contamination of the reaction mixture and the surroundings. Furthermore, the process is much simpler and can be conducted using much less equipment.

Figure 1:
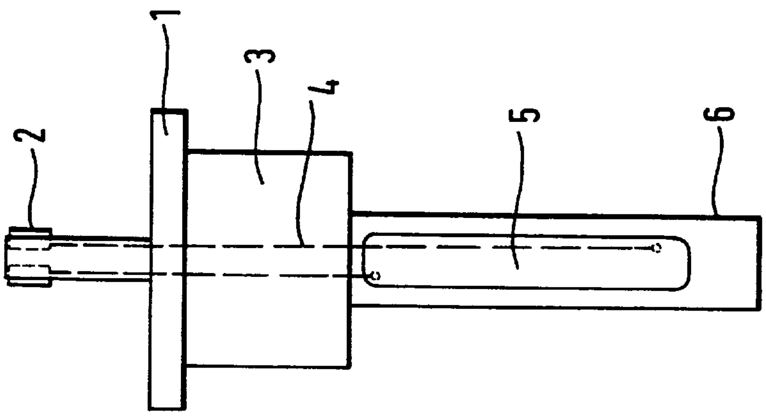
FIG. 1 illustrates a lid according to the invention with an integrated heating element.

FIG. 1 illustrates a lid (1) according to the invention with an integrated heating element. It is perceivable that the lid has a closable part which is fitted exactly to the shape of the opening of the vessel which is to be sealed. The seal extends to a plastic mounting (6) for the heating element (5). The heating element is secured to the surface of this plastic mount in such a manner that the power supply wiring (4) for the heating element can rest inside the plastic mount or seal and at one end electrical contacts (2) extend far enough to a power supply.

The lid is shown in FIG. 2 such that it is actually set onto a vessel. The outer dimensions for a vessel are displayed in FIG. 2 and are those for the lid shown in FIG. 1. These external dimensions are suitable for the execution of the process of invention eg for the amplification process but can however be easily adjusted to differing amounts of liquid in particular by a professional skilled in the art. The number 7 in the figure denotes the vessel.

Figure 3:
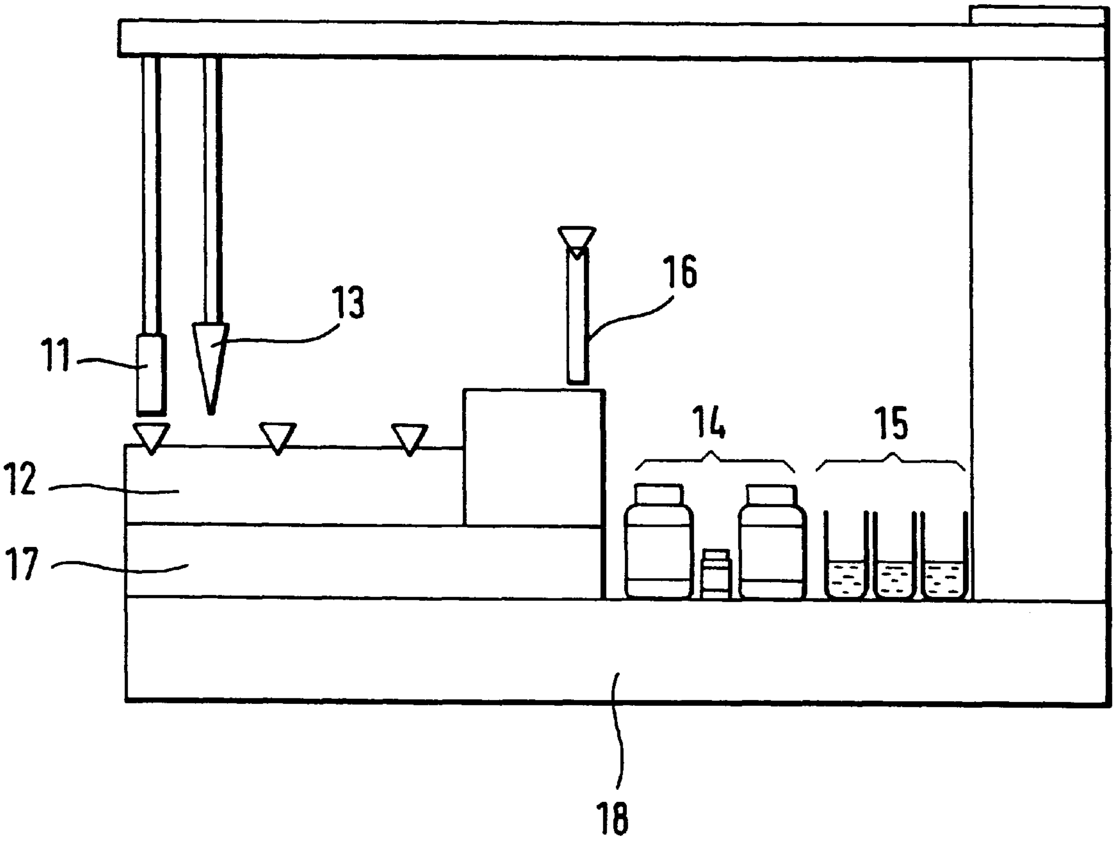
FIG. 3 shows a system according to the invention in which a preparation of nucleic acid containing liquids is conducted.

In FIG. 3 a system according to the invention with a sample preparation module 17 is shown, the said being one in which a preparation of nucleic acid containing liquids for amplification can be carried out and in which the amplification itself can be conducted. In this figure the top handling arm (lid handling arm 11) can grip the lid shown in FIG. 1 (top 1) and put this onto reaction vessels (disposable devices 12). Furthermore, contacts for the electricity supply to the lid heater are integrated into the top handling arm. With the aid of the pipetting unit and pipette tips (disposable tips 13), reagents 14 and/or sample liquid 15 can be transferred to the reaction vessel 7 (disposable device 12 in this case). As soon as the lid of the invention is spent, it can be transferred to the waste bin 16 (solid phase disposable with top). All steps involved are preferably conducted in equipment which allows movement in all 3 dimensions (x,y,z) and in which pipetting stages and transport steps can be executed (e.g. laboratory robot 18).

Figure 4:
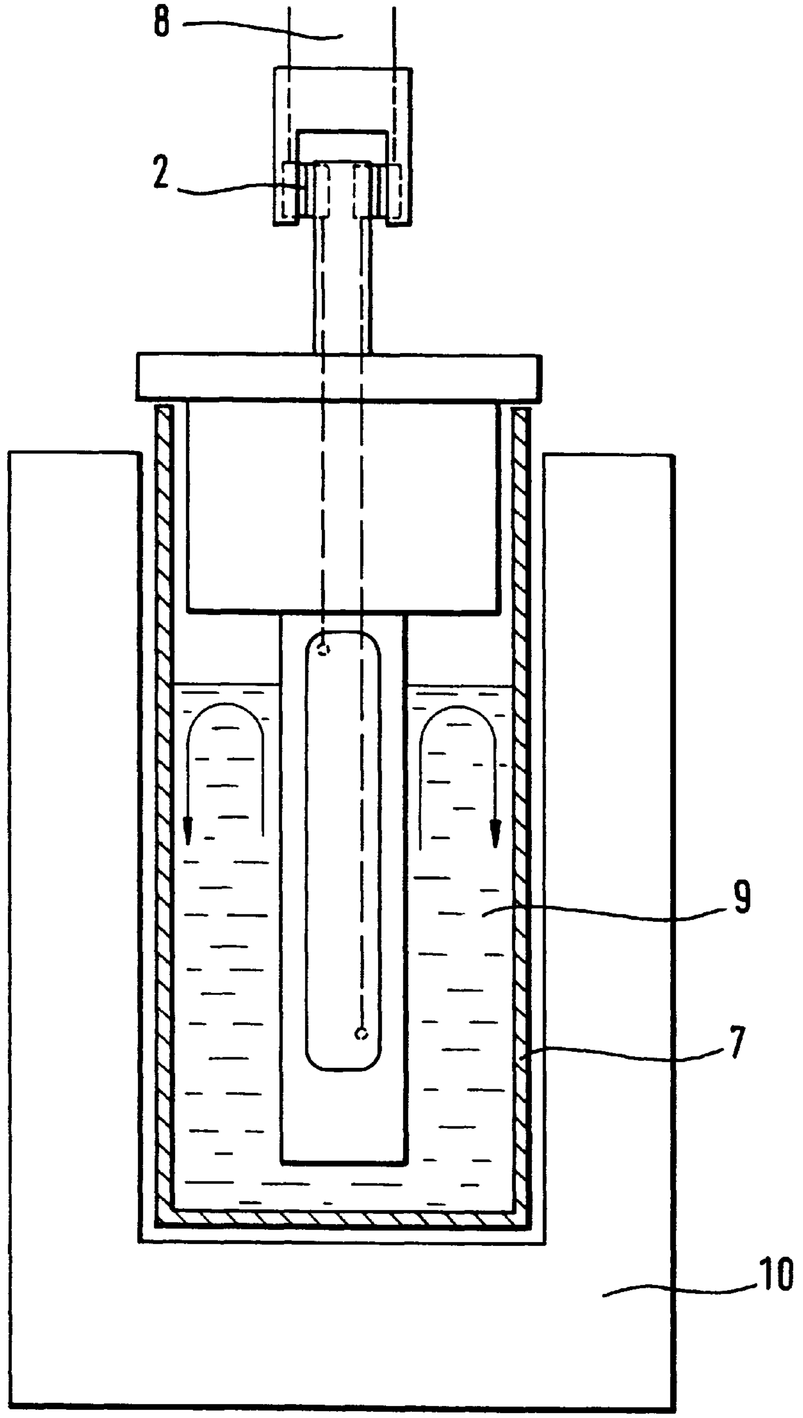
FIG. 4 shows a vessel disposed in a cooling element.

FIG. 4 illustrates a system with a power supply (8), electrical contacts (2), a vessel (7) contained within a cooling element (10), and a reaction mixture (9) which is mixed by the development of heat by the heating element in a convective manner, as indicated by the arrows.

Figure 5:
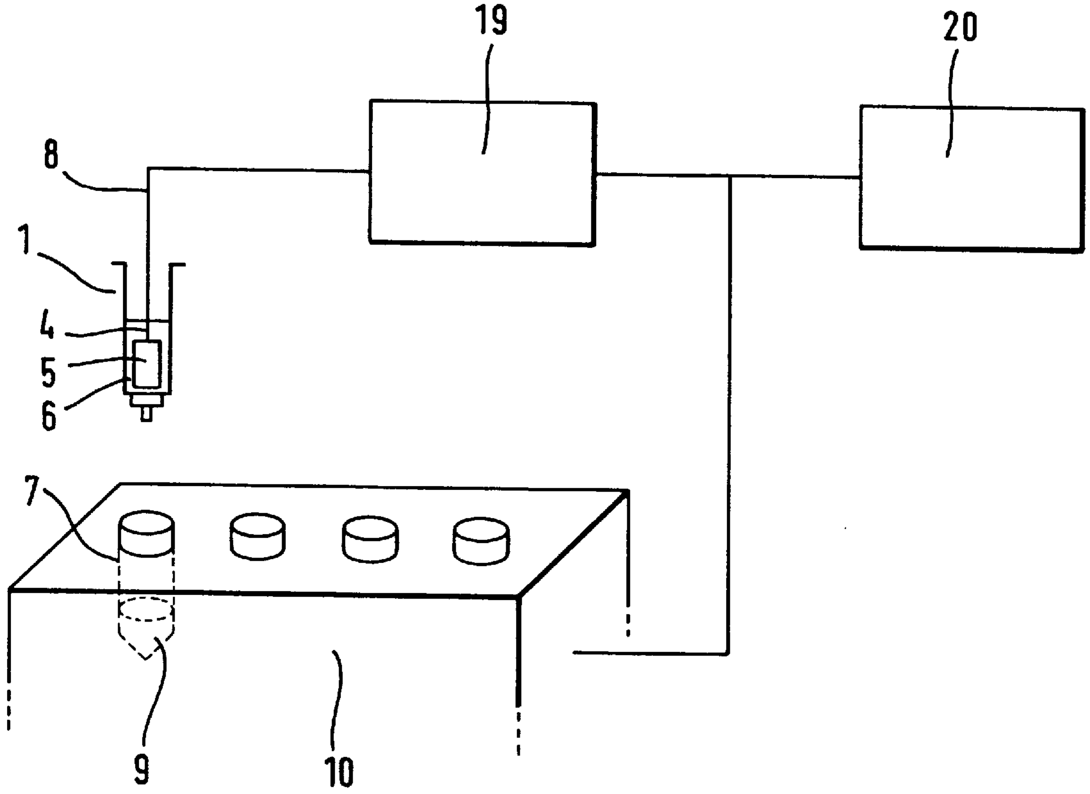
FIG. 5 shows the experimental setup of example 3.

FIG. 5 shows schematically a system for conducting the experiment including a temperature adjustment treatment. Control unit (19) controls the heating element (5), while computer (20) is used for the control of and calculations for the entire process.

Reference Numerals

1. Lid with disposable heating element
2. Electrical contacts
3. Lid seal
4. Electrical supply wiring for the heating element (moulded inside the plastic)
5. Heating element (gold foil)
6. Plastic mount for the heating element
7. Vessel
8. Connection for power supply
9. Reaction mixture
10. Cooling element
11. Lid handling unit (picking-up, taking-off, putting-on of lid, electricity supply via contacts)
12. Disposable device (contains a plurality eg 16 vessels, which are linked to each other)
13. Pipette tips on a pipetting arm of the device
14. Reagents in vessel
15. Sample liquid in vessel
16. Waste bin for lid
17. Sample preparation module (receiver for vessels, thermostat block)
18. Laboratory robot (control of transport and thermostatting steps and operating procedure)
19. Control unit for the heating element
20. Computer for the control of and calculations for the whole process

EXAMPLE 1

Establishment of a system to conduct a DNA analysis

The system is comprised of a waterbath which is thermostatted at 57° C.

Above the waterbath is an apertured plate secured at a certain distance and which enables the reaction vessel as shown in FIG. 2 to extend into the water to an extent of about half its length. A rim on the vessel prevents the slipping of the vessel into the water. The aperture plate receival bores are only marginly larger than 8 mm. The plastic vessel is made of propylene having a wall thickness of 0.4 mm (FIG. 2).

The inserted heating element is shown schematically in FIG. 1. It is an injection-moulded plastic component which incorporates a 20 μm thick gold foil and wiring integrated in such a manner that the liquid can wet the gold foil on one side.

EXAMPLE 2

Execution of a DNA-analysis under conditions of static temperature gradient

1. Sample preparation/DNA Isolation

Human leucocytes were isolated from whole human blood using the following method and employing the QIAamp Blood Kit (Cat. No. 29104), Quiagen (FRG, P.O. Box., 40719 Hilden).

200 μl EDTA-anti coagulated whole blood, 25 μl proteinase-K solution (19 mg/ml) and 200 μl degraded sample were pipetted into a 2 ml Eppendorf container. The sample was immediately shaken with Vortex® to resuspend the pellet which was forming in solution. The sample was heated for 10 minutes at 70° C., cooled to room temperature. 210 μl isopropanol were then added to the solution. The sample was transferred to a QIAamp "spin-column". The spin-column is a centrifuging device/tube which is open downwards and to which a glass fiber fleece is attached at the bottom.

The spin-column was inserted into a sample collection container (2 ml Eppendorf container) and centrifuged in a benchtop centrifuge at 6000×g for 1 minute. The filtrate was discarded and 500 μl washing buffer was pipetted into the spin column. It was then centrifuged 1 minute at 6000×g. The filtrate was discarded and the washing procedure was repeated.

Thereafter 200 μl elution solution (10 mM Tris/HCl, 1 mM EDTA, pH 8. was pipetted into the spin column and the bound DNA was eluted out of the glass fiber felt after renewed centrifugation (1 minute, 6000×g).

The purified DNA was characterised using gel electrophoresis and photometry (absorbance maxima at 260 nm and 280 nm). Typically 6 μg DNA in 200 μl elution solution (approx. 30 ng DNA/μl) having an extinction coefficient A60/270 from 1.7–1.9 (an extinction of 1000 mE at 260 nm corresponds to a sample DNA content of 50 ng/μl) were obtained from 200 μl whole blood (approx. 5×10 leucocytes per ml).

The fragment size of the DNA eluted was between 1 and 50 Kbp and mainly between 20 and 40 Kbp as determined using gel electrophoresis (1% agarose gel, ethidium bromide staining).

2. Amplification/DNA replication

A sequence from the human-tPA-gene (tPA=tissue-type plasminogen activator) was amplified using two specific primers. The sequences of the primers employed were:

Forward (i.e. upstream) 5'-AGA CAG TAC AGC CAG CCT CA-3'[SEQ ID No: 1]

Reverse (ie downstream) 5'-GAC TTC AAA TTT CTG CTC CTC-3'[SEQ ID No: 2]

A 375 bp length amplified segment results using these primer pairs.

The following mastermix was pipetted into the polypropylene (PCR)-reaction vessel described above:

10 μl 10 fold PCR-buffer with $MgCl_2$ (100 mM Tris/HCl pH 8.9; 500 mM KCl, 15 mM Mg $Cl_2$)

2 μl 10 mM dNTP-mix (ie 10 mM dATP, dGTP, dCTP and dTTP each)

0.5 μl Taq-polymerase (5 U/μl)

1 μl Forward primer (30 μM, for sequence see above)

1 μl Reverse primer (30 μM, for sequence see above)

82.5 μl autoclaved, double-distilled water

All the reagents used in the amplification (except for the primer) are out of the PCR Core Kit (Cat. No. 1578 553) from Boehringer Mannheim.

The mastermix was placed briefly on a Vortex® stirrer, then centrifuged in a benchtop centrifuge. 3 μl of sample containing DNA (from point 1, DNA content approx. 30 ng/μl) were pipetted to the mastermix. The PCR vessel was placed in a heating/cooling block of the invention and sealed with a disposable heating element containing lid.

The heating element was arranged in such a manner that the resistance wire extended about two thirds of the way into the PCR mix. The heating element was connected to the electricity supply and the PCR mix incubated for 0.5 hours such that the resistance wire was kept at a temperature of 95° C. and the tube inner wall attained a temperature of 58° C.

After completion of the amplification, the PCR-mix was analysed according to point 3.

3. Analysis of the amplified DNA

10 μl of the amplified PCR sample were applied to the application site of a 1% agarose gel described in point 2. 800 ng of Boehringer DNA Langen standard VI (Cat. No. 1062 590, fragment size 2176 bp to 154 bp) were applied.

The gel was developed in an electric field for 2 hours and then analysed on a UV table.

In the presence of human leucocyte DNA in the mastermix, an intense DNA band was visible in the gel (375 bp) and was located between the 394 bp band and the 298 p-band of the Längenstandard VI.

EXAMPLE 3

Temperature adjustment treatment with time-variable temperature gradients

The aim of the experiment was determination and optimalisation of a periodically varying temperature gradient using the system of the invention. For these purposes a test tube made of polypropylene and filled with 300 μl autoclaved, double distilled water was used and inserted in the metal thermostat block which was cooled with a Peltier element. A commercially available Pt24-Chip was integrated into the lid which simultaneously served the heating element and the temperature probe. The heating element extended into the water. In a neighbouring test tube the temperature setting of the thermostat block was monitored using a M 4011BBC temperature sensing device. The experimental set up is depicted in FIG. 5. The unit was operated using varying temperature intervals. The in operation time is defined as the time interval in which the heating is active and the out of operation time was defined as the time interval between the heating cycles. The results of the tests are given in FIGS. 6 to 12. It is evident that the test run according to FIG. 12 does not facilitate a sensible temperature adjustment treatment because the time intervals are probably long enough for rehybridization of the nucleic acids. On the basis of these tests a professional skilled in the art can determine the best conditions for his own special system (special geometry, heating rate etc.).

TABLE 1

Figure 6:
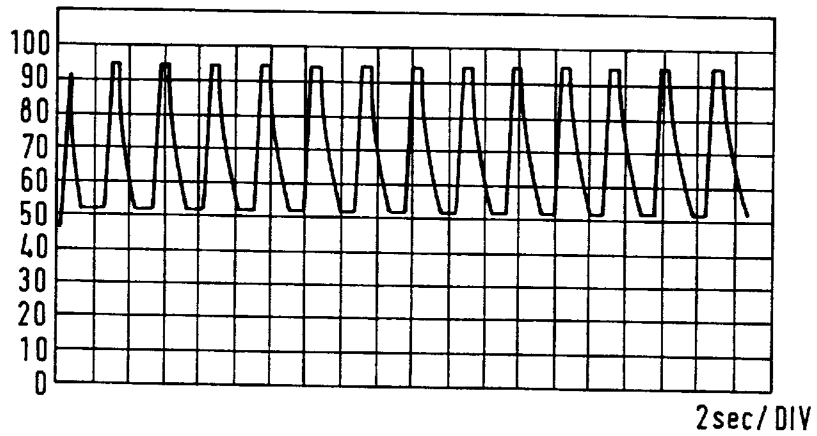
FIGS. 6 through 12 show the results of test runs according to example 3.
Figure 7:
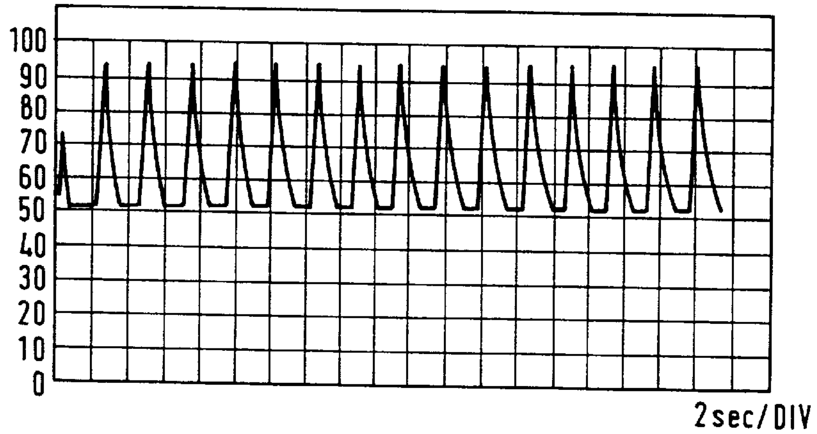
Figure 8:
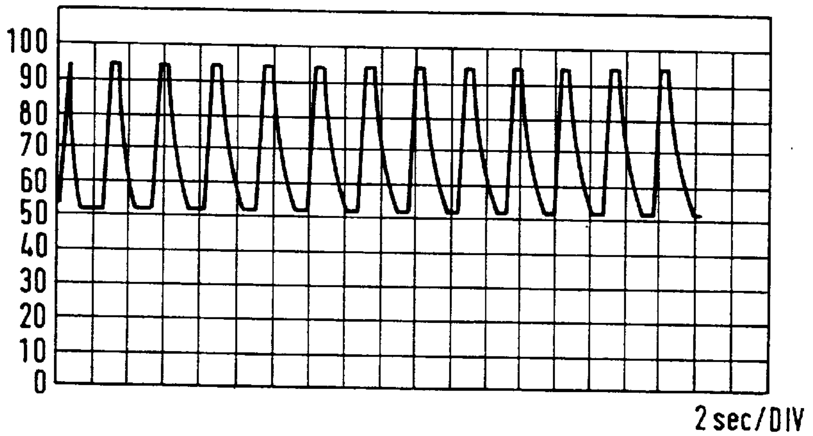
Figure 9:
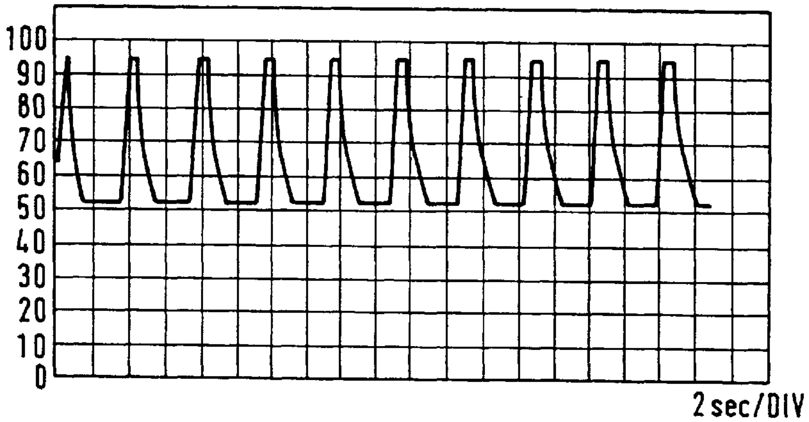
Figure 10:
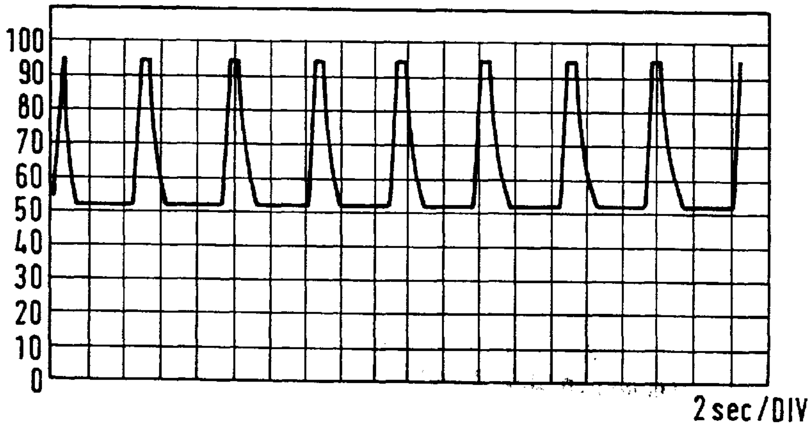
Figure 11:
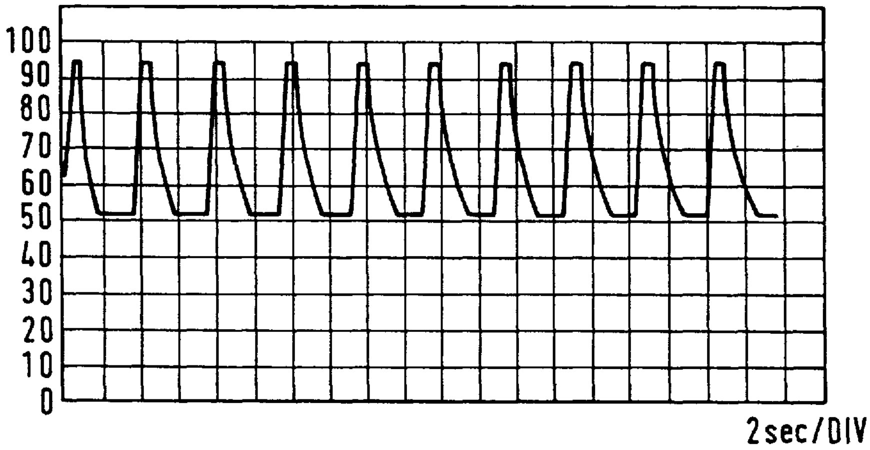
Figure 12:
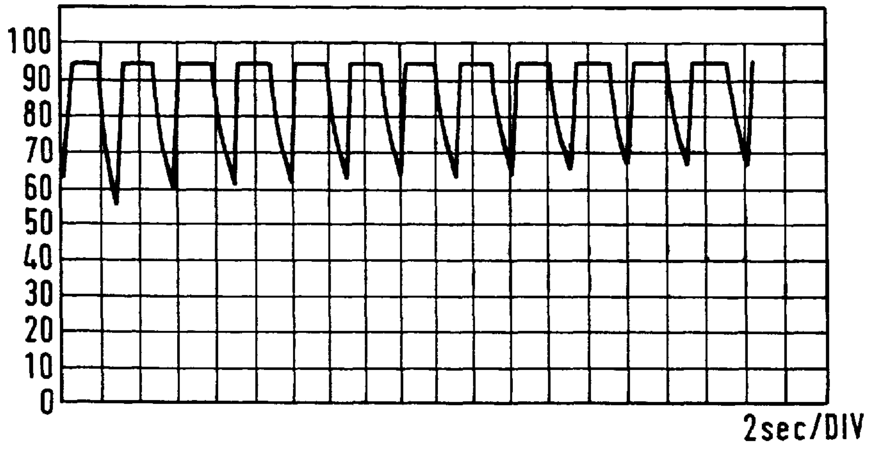

| Stand Temp./° C. | Measured Temp./° C. | On/ms | Off/ms | FIG. |
|---|---|---|---|---|
| 4 | 4.9 | 800 | 2000 | FIG. 6 |
| 10 | 11.0 | 400 | 2000 | FIG. 7 |
| 10 | 10.6 | 800 | 2000 | FIG. 8 |
| 10 | 11.0 | 800 | 3000 | FIG. 9 |
| 10 | 10.9 | 800 | 4000 | FIG. 10 |
| 20 | 20.2 | 800 | 3000 | FIG. 11 |
| 20 | 20.5 | 2000 | 1000 | FIG. 12 |

We claim:

1. A system for the temperature adjustment treatment of a nucleic acid-containing liquid in a vessel, comprising:

(a) a vessel for the liquid, (b) a vessel lid which is placeable in a closing relationship with the vessel, (c) thermostat element which is in a temperature-controlling relationship with the liquid in the vessel, and (d) a disposable heating element which is an integral component of the vessel lid, and is at least partially in contact with the liquid during at least a part of the temperature adjustment treatment of the liquid.

2. A system as claimed in claim 1, wherein the thermostat element is a cooling element.

3. A system as claimed in claim 2, wherein the vessel has an outer surface and the cooling element is fitted to the outer surface.

4. A system as claimed in claim 2, wherein the cooling element is at least partially in contact with the liquid during at least a part of the temperature adjustment treatment of the liquid.

5. A system as claimed in claim 2, wherein the cooling element is of metal.

6. A system as claimed in claim 2, wherein the cooling element comprises a water bath into which the vessel is at least partially submerged.

7. A system as claimed in claim 1, wherein the disposable heating element is of metal or graphite.

8. A system as claimed in claim 1, wherein the disposable heating element is of gold.

9. A system as claimed in claim 1, wherein the disposable heating element is molded into the vessel lid.

10. A system for the temperature adjustment treatment of a plurality of nucleic acid-containing liquids in a plurality of vessels, comprising:

(a) a plurality of vessels, each for containing one of the plurality of liquids, (b) a plurality of vessel lids, each of which is placeable in a closing relationship with one of the plurality of vessels, (c) at least one thermostat element which is in a temperature-controlling relationship with the plurality of liquids, and (d) a plurality of disposable heating elements, each of which is an integral component of the plurality of vessel lids, and is at least partially in contact with one of the plurality of liquids during the temperature adjustment treatment of plurality of liquids.

11. A system as claimed in claim 10, wherein the thermostat element is of metal, and has a plurality of bore holes defined therein for receiving the plurality of vessels.

* * * * *

SEQUENCE LISTING

```
(1) GENERAL INFORMATION:

   (iii) NUMBER OF SEQUENCES: 2


(2) INFORMATION FOR SEQ ID NO: 1:

     (i) SEQUENCE CHARACTERISTICS:
          (A) LENGTH: 20 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "Oligodesoxyribonucleotide"

   (iii) HYPOTHETICAL: NO

    (xi) SEQUENCE DESCRIPTION: SEQ ID NO: 1:

AGACAGTACA GCCAGCCTCA                                           20


(2) INFORMATION FOR SEQ ID NO: 2:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "Oligodesoxyribonucleotide"

   (iii) HYPOTHETICAL: NO

    (xi) SEQUENCE DESCRIPTION: SEQ ID NO: 2:

GACTTCAAAT TTCTGCTCCT C                                         21
```